United States Patent [19]

Vaughan et al.

[11] 4,399,441
[45] Aug. 16, 1983

[54] APPARATUS FOR REMOTE TEMPERATURE READING

[75] Inventors: Richard Vaughan, Maroubra; Peter H. Cole, West Lakes, both of Australia

[73] Assignee: Unisearch Limited, Kensington, Australia

[21] Appl. No.: 226,518

[22] Filed: Jan. 19, 1981

[30] Foreign Application Priority Data

Jan. 25, 1980 [AU] Australia .............................. PE2148

[51] Int. Cl.$^3$ .......................... G01S 9/56; G01S 13/74
[52] U.S. Cl. ................................. 343/6.5 SS; 128/736
[58] Field of Search ..................... 343/6.5 SS; 128/736

[56] References Cited

U.S. PATENT DOCUMENTS

| | | | |
|---|---|---|---|
| 3,341,845 | 9/1967 | Deman | 343/6.8 LC X |
| 3,453,546 | 7/1969 | Fryer | 128/736 X |
| 3,706,094 | 12/1972 | Cole et al. | 343/6.5 SS |
| 3,798,641 | 3/1974 | Preti | 343/6.5 SS |
| 3,893,111 | 7/1975 | Cotter | 128/736 X |
| 4,087,791 | 5/1978 | Lemberger | 343/6.5 SS X |
| 4,138,998 | 2/1979 | Nowogrodzski | 128/736 X |
| 4,253,469 | 3/1981 | Aslan | 128/736 |

Primary Examiner—Theodore M. Blum

[57] ABSTRACT

An apparatus for remote temperature reading particularly for the reading of the temperature of an article or animal at a distance by means of an electromagnetically interrogatable label attached to or implanted in the article or animal the label being constructed to be capable of receiving an electromagnetic signal from a transmitter, converting the signal to a surface acoustic wave, passing the wave over a path on the label, reconverting the surface acoustic wave to an electromagnetic signal and retransmitting it to a receiver. The path of the surface acoustic wave is of a material such that the time of travel of the surface acoustic wave over the path is a function of the temperature of the path and thus of the label. The receiver is constructed to measure the time interval between electromagnetic signals produced by the passage of the surface acoustic wave past a transducer or transducers in the path and thereby provide an output indicative of the temperature of the environment of the label. It is preferred that the label includes a plurality of transducers at coded locations along the path arranged for retransmitting to the receiver a coded sequence of electromagnetic signals indicative of an article or animal to which the label is affixed or in which it is implanted in the manner described in U.S. Pat. No. 3,706,094.

5 Claims, 10 Drawing Figures

APPARATUS FOR REMOTE TEMPERATURE READING

The present invention relates to an apparatus for remote temperature reading and more particularly for the reading of the temperature of an article or animal at a distance by means of an electromagnetically interrogatable label attached to or implanted in the article or animal.

One object of the invention is to provide an apparatus to enable such temperature readings to be made. A further object is to provide, in certain forms of the invention, a facility not only for reading the temperature of the article or animal but of obtaining information as to the identity of the article or animal.

Attempts have recently been made by the livestock industry in the United States of America to develop a system of electronic identification of cattle to be used on a national basis. Functional specifications for the proposed national system have been drawn-up by the U.S. Livestock Conversation Institute. These specifications call for implantable transponders readable at a range of three meters, and returning not only an identification code, but also a reading of the subdermal temperature of the animal for disease detection purposes. Temperature is required to be read over a span of 30° to 45° C., with an accuracy of ±0.5° C. and a reproducibility of ±0.1° C. Responders employing transistorised oscillators whose frequency is varied by temperature sensitive thermistors have been described previously, see, for example, the Oct. 1, 1977 to Sept. 20, 1978 progress report LA-7642-PR on Electronic Identification by the Los Alamos Scientific Laboratory. Such transistorised responders are complex and too expensive for general use by the livestock industry. The present invention can with advantage be applied to meeting these requirements.

So far as effecting the identification of articles and animals is concerned this aspect of the present invention is derived from an invention described in U.S. Pat. No. 3,706,094 entitled "Electronic Surveillance System". That system employs a passive coded label based on surface acoustic wave technology to return an information-bearing electromagnetic reply signal in response to excitation by a radio-frequency pulse. The essential features of the system are the low cost of the purely passive labels, and the freedom of orientation and visibility constraints between the labels and the code reading apparatus. This combination of characteristics enables the system to be applied to a wide range of articles which because of their uncontrolled shape cannot be economically sorted by other systems using such means as optical bar codes, fluorescent paint, magnetic strips, active transponders employing transistors, etc. Potential application areas are the sorting of postal parcels, local sorting and inter-line transfer of airline baggage, labelling of frozen foodstuffs, error-free identification of livestock and carcasses in primary industry, etc.

The present invention is based on an appreciation of the fact that a passive label utilizing surface acoustic wave technology can be used to provide an unambiguous reading of the temperature of an article or animal to which the label was attached and that, where desired, such a function could be combined with the identification function of such a label in the manner described in the abovementioned patent specification. The invention is thus applicable in a basic form for use wherever remote electromagnetic reading of the temperature of the label's environment is required as for example in implantable biomedical temperature sensors and also in a more complex form in situations in which a remote electromagnetic reading of an identifying label together with a reading of the temperature of the label's environment is required.

The present invention consists in apparatus for remote temperature reading comprising transmitter means for transmitting electro-magnetic signals, label means adapted for attachment to or implantation in an article or animal for receiving a signal from said transmitter means and for retransmitting a reply, and receiver means for receiving and processing the reply; said label means including antenna means for receiving said transmitted signal, transducer means for converting said electromagnetic signal to a surface acoustic wave, a path on said label over which said surface acoustic wave travels, the time of travel of said surface acoustic wave over said path being a function of the temperature of the path, the same or further transducer means being arranged to convert said surface acoustic wave to a first electromagnetic signal after it has travelled over a first part of said path and to feed said signal to said antenna for retransmission to said receiver means and thereafter to convert said surface acoustic wave to a second electromagnetic signal after it has travelled over a second part of said path and to feed said second electromagnetic signal to said antenna for retransmission to said receiver means, said receiver means including circuitry for measuring the time interval between said first and second electromagnetic signals resulting from the passage of said surface acoustic wave over said path and for providing from said measured time interval an output indicative of the temperature of the environment of the label means. It is preferred that said label means shall include a plurality of transducer means at coded locations along the said path arranged for retransmitting to said receiver means a coded sequence of electromagnetic signals indicative of an article or animal to which the label is affixed or in which it is implanted.

In order that the nature of the invention may be better understood preferred forms thereof are hereinafter described by way of example with reference to the accompanying drawings in which.

Figure 1:
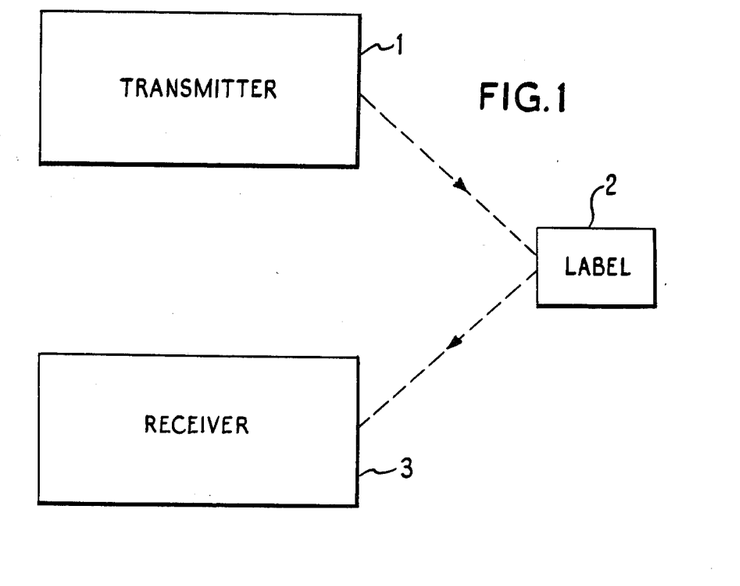
FIG. 1 is a block diagram of the sytem as a whole.

The basic components of the system are shown in the block diagram of FIG. 1. The system contains a transmitter of electromagnetic waves 1, an information carrying and temperature sensitive label 2, and a receiver of electromagnetic waves 3, all of which are operated simultaneously. The system described employs a label returning a thirty two bit identifying code plus an unambiguous readout of the temperature of the label over a range of ±9.5° C. e.g. from 28° C. to 47° C., with an accuracy approaching ±0.004° C. under normal operating conditions.

Figure 2:
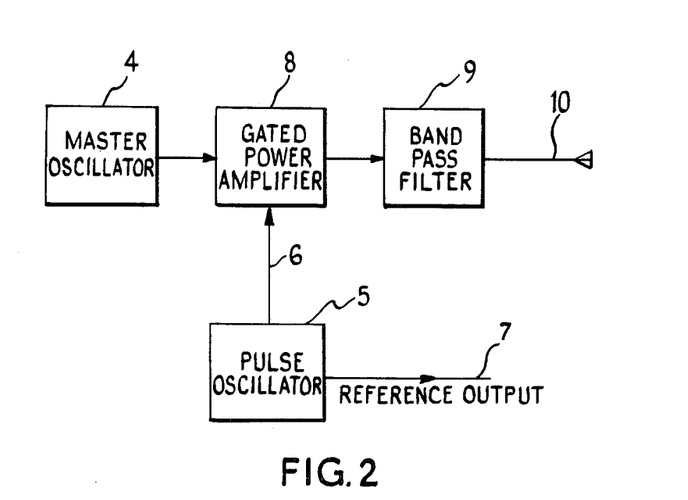
FIG. 2 is a block diagram of the transmitter unit.

Further details of the transmitter unit appear in FIG. 2. The transmitter employs standard UHF and microwave technology. The principle components and specifications are:

(a) A master oscillator 4 operating (in this example) at 915.000,000 MHz.

(b) A low frequency pulse oscillator 5 producing rectangular gating pulses of duration 20 nsec and pulse repetition frequency 505,106 Hz with a main output 6 and reference output 7 as shown.

(c) A pulsed power amplifier 8 with centre frequency 915.000,000 MHz, bandwidth 50 MHz, peak pulse output power 20 watts, pulse repetition frequency 505,106 Hz, and on/off ratio in excess of 150 decibels.

(d) An output filter 9 having a passband of 915.000,000 ±20 MHz to restrict the frequency components of the output radiation to those allowed by the relevant statutory authority.

(e) A microwave antenna system 10 which illuminates the area containing the label to be read.

Figure 3:
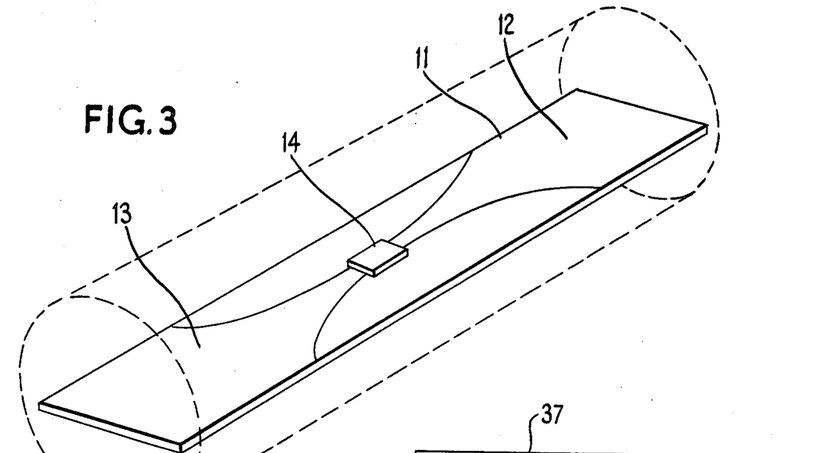
FIG. 3 is an isometric view of a label suitable for implantation in cattle.

One possible form of construction of a label suitable, for example, for implantation in cattle is shown in FIG. 3. The label consists of an antenna structure 11 in the form of a plastic card carrying copper-foil tabs 12 and 13. The responding portion of the label consists of an acoustic wave delay line element 14 electrically connected across a gap between tabs 12 and 13. Finally, the label is encapsulated for physical protection within a plastic cylinder 15 of suitable biologically inert material. The length of encapsulated label can vary from approximately 75 to 150 mm, with the smaller size being achievable with a small loss in system sensitivity.

The surface acoustic wave delay line element 14 consists of a substrate 15 having suitable piezoelectric and acoustic propagation properties, including an appropriate difference between the temperature coefficient of linear expansion of substrate 14 and the temperature coefficient of the velocity of surface acoustic wave propagation along its surface. The difference between these two temperature coefficients will be hereafter called the time-delay temperature coefficient and denoted by the abbreviation "td Tempco". In the present case a substrate consisting of a thin layer of sputtered zinc oxide on glass is used having a td Temco of approximately -60 parts per million per °C. Many other materials can however be used, including both appropriately oriented single crystal substrates and composite substrates consisting of thin layers of zinc oxide or other piezoelectric materials on glass or metal plates or foils, and such materials may be of advantage in achieving higher or lower values of td Temco for particular applications.

Figure 4:
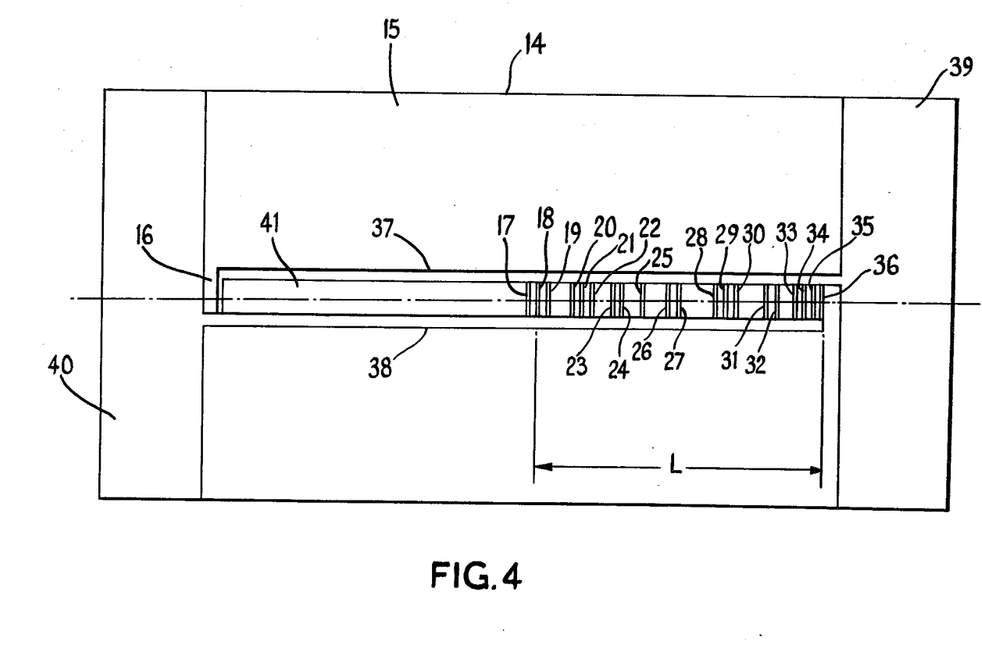
FIG. 4 is a view of the surface acoustic wave delaying forming part of the label.
Figure 5:
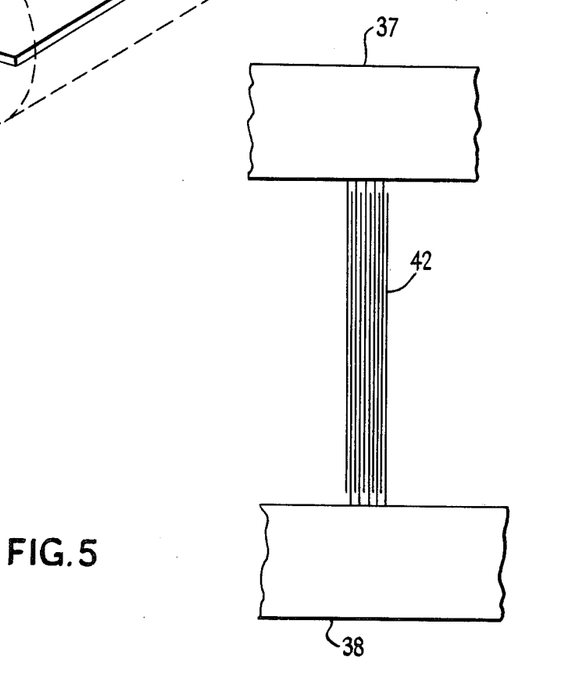
FIG. 5 shows details of one of the transducers of the surface acoustic wave delay line.

The reply code of the label is encoded on substrate 15 in the form of the spatial pattern formed by a conducting electrode array deposited on the substrate surface. Details of the spatial pattern appropriate to the 32 bit binary code 1110 0111 0110 1001 1000 1110 0110 1111 are shown in FIG. 4. The array comprises an end transducer 16 and a set of coding transducers 17, 18, 19, 20, 21, 22, 23, 24, 25, 26, 27, 28, 29, 30, 31, 32, 33, 34, 35 and 36. A coding transducer is present or absent according to whether a binary "1" or a binary "0" digit is required at that particular bit position in the reply code. All transducers are connected in parallel between conductors 37 and 38. Conductors 37 and 38 join to bonding pad areas 39 and 40 respectively. Bonding pad areas 39 and 40 provide for mechanical and electrical connection, by means of electrically conducting epoxy, of the surface acoustic wave delay line element 14 to tabs 12 and 13 of antenna structure 11 as shown in FIG. 3. The details of one of the transducers are shown in FIG. 5, the transducer consisting of a number of "finger-like" electrodes 42 connected alternatively to conductor 37 or to conductor 38. The centre-to-centre spacing of the electrodes in this example is approximately 2 $\mu$m; the precise distance is adjusted to be one-half of a wavelength of a surface acoustic wave at the operating centre frequency of 915 MHz. The first and last coding transducers of the coding transducer set, i.e. transducers 17 and 36 in FIG. 4, are always present, and in the present example are separated by 2.790 mm indicated at L and serve the combined purposes of establishing label reply-code signal levels, and of providing the temperature measuring capability of the label.

The remaining 30 code bit positions are available for coding of the required label identifier information by the presence or absence of a transducer as discussed above. In the present example 19 such transducers, viz. transducers 18, 19, 20, 21, 22, 23, 24, 25, 26, 27, 28, 29, 30, 31, 32, 33, 34 and 35 in FIG. 4, have been used to provide the code 1110 0111 0110 1001 1000 1110 0110 1111. The invention is not limited to the particular number, i.e. 32, of code bits chosen in the present example. A smaller of larger number of code bits may be used according to the amount of identifier information to be encoded. The size of the surface acoustic wave delay line element 14 scales in size approximately in proportion to the total number of code bits required, and element 14 can be made much smaller if temperature measurement and readout only is required.

As stated above, in the present example a bit position is coded as a binary "1" or as a binary "0" according to whether a transducer is present or absent at that position. As an alternative method, all elements may be present, but those elements in positions where a binary "0" is required may be either left unconnected to one or both of conductors 37 and 38 at time of manufacture, or connected to conductors 37 and 38 in such a way that the required code can be impressed on the label by the user by severing connections to conductor 37 or to conductor 38 as required.

In operation, the label received the pulsed electromagnetic energy via its antenna 11, and energises all transducers connected to conductors 37 and 38. Each connected transducer launches surface acoustic waves travelling in directions parallel to centre line CC of FIG. 4. After a time equal to the propagation time of such waves along the blank portion 41 of the surface acoustic wave delay line element 14, the electroacoustic surface waves are reconverted to electromagnetic energy which is then reradiated as electromagnetic waves via antenna 11. This reradiatted electromagnetic energy is picked up and processed by the receiver 3.

Figure 6:
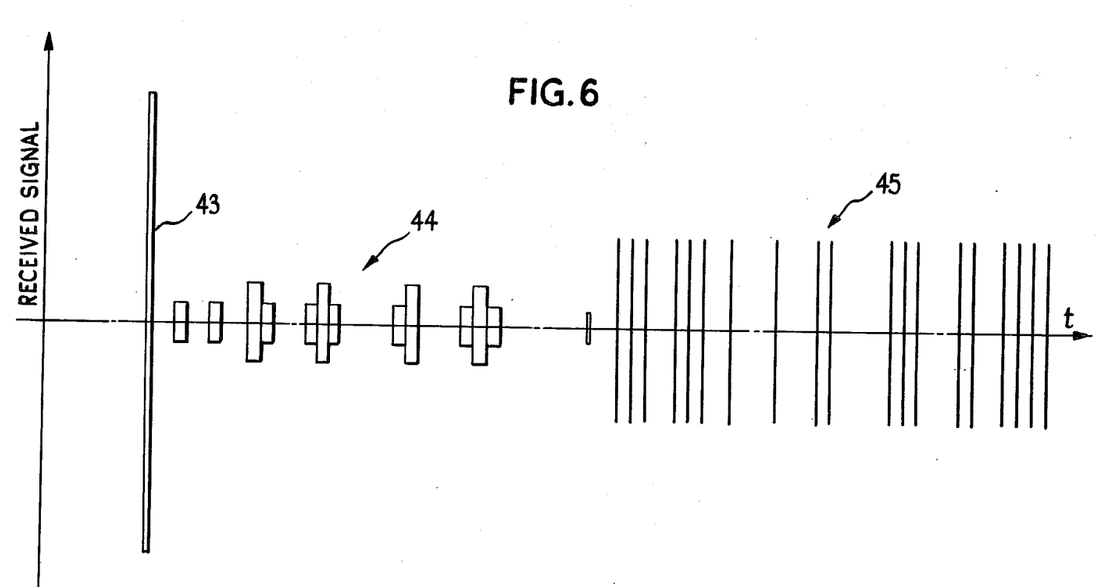
FIG. 6 is a diagram of the sequence of pulses which arrive at the receiver.

A diagram of the sequence of pulses which arrive at the receiver is shown in FIG. 6. The sequence consists of a large amplitude pulse 43 arriving directly from the transmitter, followed by a series of unwanted interference pulses 44 which result from the propagation of surface acoustic waves between various members of the members of the code transducer set 17 through to 36, followed by the wanted set of pulses 45 which result from propagation of surface acoustic waves between the end transducer 16 and the members of the code transducer set 17 through to 36 in sequence. It is this last group of pulses which is free from interference, and which is processed by the receiver 3 in the manner described below to yield both the identified code of the label and the reading of the temperature of the label as determined by the environment in which it is situated.

Figure 7:
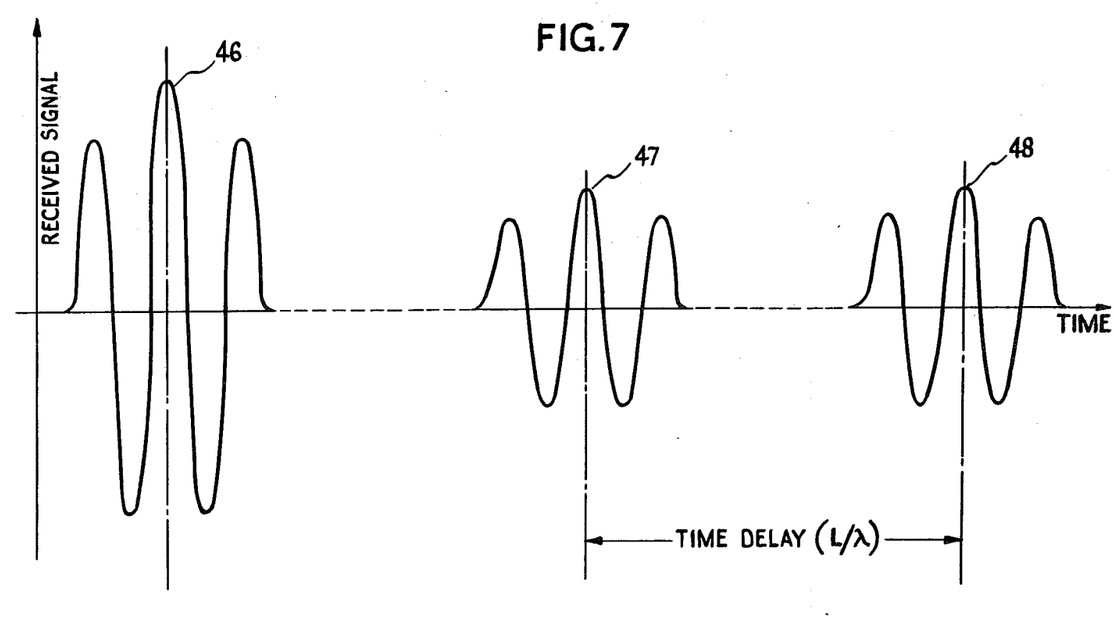
FIG. 7 is a diagram of the radio frequency ("RF") wave forms associated with the direct transmitter pulse together with the wanted reply pulses from the first and last code transducers.

The method of temperature measurement may be understood by reference to FIG. 7 which shows in diagrammatic form only the radio-frequency ("RF") waveform 46 associated with the direct pulse 43, together with the RF waveforms 47 and 48 associated with the first and last pulses respectively of the wanted set of pulses 45, RF waveforms 47 and 48 thus resulting from propagation of surface acoustic waves between the end transducer 16 and code transducer 17 and 36 respectively. The phase difference $\phi$ between RF waveforms 47 and 48 is equal to $2\pi(L/\lambda)$ rads, where L is the centre-to-centre spacing between transducers 17 and 36 and $\lambda$ is the surface acoustic wave wavelength for waves propagating between transducers 17 and 36. L and $\lambda$ are known functions of temperature determined by the material of substrate 14; measurement of $\phi$ therefore provides a measurement of the temperature of substrate 14, i.e. of the temperature of the label as determined by its environment. It may be shown that the rate of change of $\phi$ with temperature is equal to $2\pi(L/\lambda)$ rads times the time delay temperature coefficient td Tempco previously defined. For the present example the temperature variation of $\phi$ is approximately $2\pi \times (2790 \mu m/3.28 \mu m) \times -60 \times 10-6$, i.e. 0.32 rads per °C., giving unambiguous temperature measurement over the range 28° to 47° C. with an accuracy of approximately ±0.004° C. at the normal operating signal-to-noise ratio ("S/N ratio") of 57 db, see below. The requirements of the U.S. Livestock Conservation Institute discussed above are thus adequately met.

Figure 8:
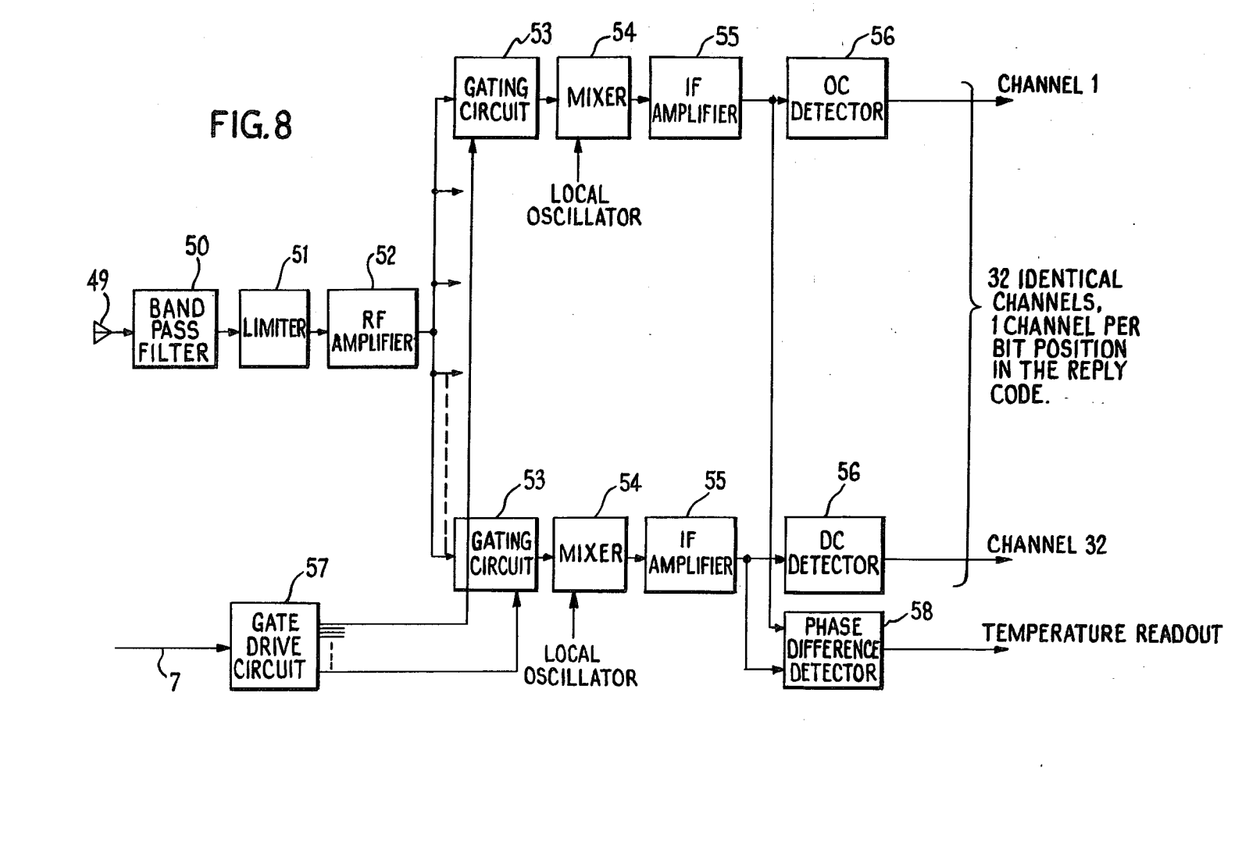
FIG. 8 is a block diagram of the receiver.

The various components of the receiver 3 are shown in block diagram form in FIG. 8. The directional antenna 49 is similar in design to transmitter antenna 10. A band pass filter 50 serves to reject possible radio frequency interference from sources unrelated to the system. A limiting device 51 protects the receiver from saturation or overload from the large amplitude transmitter pulse. A low noise RF amplifier 52 provides amplification of the received pulse sequence, and is designed in such a way that, in this example, 32 parallel outputs are provided, one output for each bit position in the reply code. Each of the 32 outputs from RF amplifier 52 drives one of the 32 identical signal processing channels only 2 of which are shown in FIG. 8 for clarity, each of the 32 outputs being fed initially to one of 32 gating circuits 53. These gates are controlled by a gate drive circuitry 57, which is synchronised with the transmitter pulse via a signal brought from the transmitter via reference line 7. The gate drive circuit 57 provides 32 output pulses each with a width equal to the width of the transmitter pulse, i.e. 20 nanosec. in this example. The 32 output pulses from gate drive circuit 57 control gates 53 in such a way that successive gates 53 open to pass reply pulses from pulse set 45 corresponding to successive bit positions 1 to 32 of the reply code. The outputs from gates 53 are then down-converted in mixers 54 by beating with a 914.999,000 MHz offset local oscillator phase-locked to master oscillator 4, and the resulting 1000 Hz intermediate frequency ("IF") signals amplified by narrow-band IF amplifiers 55. The outputs from IF amplifiers 55 are full-wave rectified by precision DC detectors 56, the outputs from DC detectors 56 providing the 32 bits of the reply code. As stated, bits 1 and 32 produced by code transducers 17 and 36 respectively are always binary "1's", and serve the combined purpose of establishing label reply-code signal levels, and of providing the temperature measurement capability of the label by means of measurement of the phase difference $\phi$ between RF waveforms 47 and 48 respectively associated with them. Since the phase of an RF waveform is preserved during frequency down-conversion, phase difference $\phi$ can be readily measured by a phase difference detector 58 having reference inputs taken from the outputs of the IF amplifiers 55 of bit channels 1 and 32, as shown in FIG. 8. Various standard phase difference detector circuits having an unambiguous phase measurement range of $\pm \pi$ rads can be used for phase difference detector 58, phase measurement being greatly simplified by the overall system design shown in FIG. 8 whereby phase measurement can be performed at IF frequency, i.e. 1000 Hz in the present example, using simply non-critical low-frequency circuitry.

The outputs of the receiver described above can be fed to a wide range of standard display devices not shown in FIG. 8 to display the identifier code and the temperature of the label is required. The design of such readout devices follows well established procedures.

Calculations show that the power losses occurring in various parts of the overall transmission path from transmitter to receiver are:
 (a) Electromagnetic propagation loss from transmitter antenna to label antenna: 33 db.
 (b) Electromagnetic to electroacoustic conversion loss: 44 db.
 (c) Electroacoustic propagation loss: 4 db.
 (c) Electroacoustic to electromagnetic conversion loss: 37 db.
 (e) Electromagnetic propagation loss from label antenna to receiver antenna: 33 db.
The overall transmission path loss is 151 db.

The noise bandwidth of the receiver is determined by the passbands of IF amplifiers 55 and is set at 3 Hz. The input noise level of the receiver, allowing for 1 db total loss through bandpass filter 50 and limiter 51 together with 6 db noise figure of RF amplifier 52, is $-192$ db W. The input signal level at the receiver is $-135$ db W. The signal to noise ratio at the receiver is thus 57 db and the system is not receiver noise limited. In particular it may be shown that the error $\Delta\phi$ in phase difference measurement by phase difference detector 58 is approximately equal to the reciprocal of the square root of the receiver signal to noise ratio, i.e. $\Delta\phi$ is approximately equal to $\pm 1.41 \times 10^{-3}$ rads for a receiver signal to noise ratio of 57 db. The resulting error in measurement of label temperature is thus $\pm 1.41 \times 10^{-3}$ rads per °C., i.e. $\pm 0.004°$ C. As previously stated the requirements of the U.S. Livestock Conservation Institute discussed above are thus adequately met.

The system depends for its success in distinguishing the acoustically delayed echoes from background clutter produced by direct electromagnetic echoes. Since the acoustic time delay before arrival of the reply pulse sequence is, in this example, of the order of 1 microsecond, the relevant interferring electromagnetic echoes will be via propagation paths of length in excess of 300 meters, and will normally be negligibly small.

There are certain obvious variations from the particular example described in detail above which may be made to suit particular circumstances but which lie within the true scope and intendments of the present invention.

(a) Changes of carrier frequency from 915 MHz. The dimensions of the surface acoustic wave delay line element 14 and the electrode array deposited thereon may be scaled by change of frequency and system bandwidth as required by the technology to be employed in their manufacture or as required by statutory frequency allocation.

(b) Pulse length and pulse repetition rate may be varied to achieve a longer or a more compact code.

(c) Changes may be made in transmitter power level and in the characteristics of the transmitter, receiver and label antennas, including the use of transmitter-receiver duplexing, to provide various microwave propagation systems.

(d) As stated, a variety of piezoelectric substrate materials can be used, including both appropriately oriented single crystal substrates and composite substrates consisting of thin layers of zinc oxide or other piezoelectric materials on glass or metal plates or foils. Magneto-strictive devices may also be used in place of or in conjunction with piezoelectric materials to accomplish the electroacoustic conversion.

(e) The transducer array structure can be modified in number and shape of the transducers, and in the manner of their connection to the label antenna.

(f) In relation to the identifying code returned by the label, coding methods other than simply binary, such as pulse height, width or position, can be used.

(g) The disposition of the various elements in the label, and the size, shape and encapsulation of the label can be varied to suit particular applications.

Figure 9:
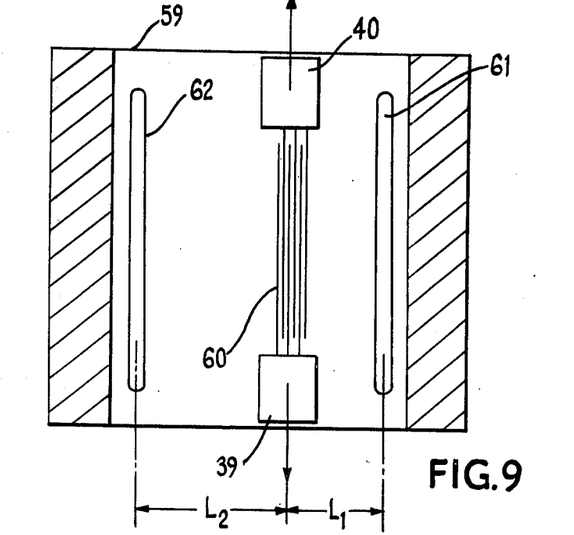
FIG. 9 shows a modified transducer array structure where only a minimum identifying code capacity is required.
Figure 10:
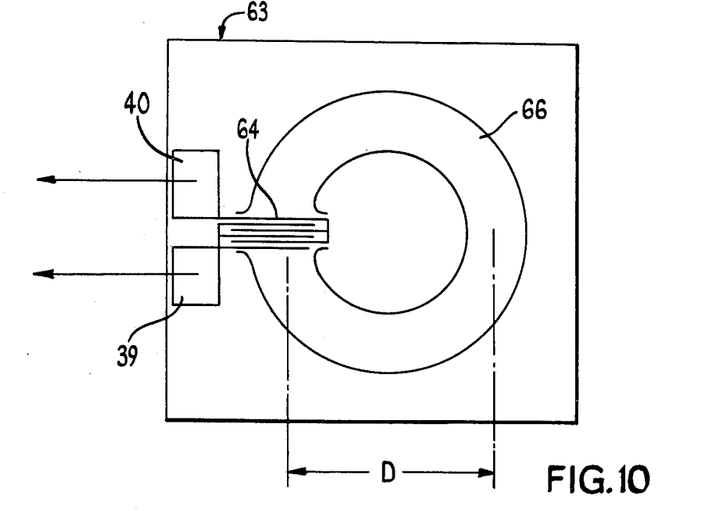
FIG. 10 shows a second modified transducer array structure where only a minimum identifying code capacity is required.

(h) The code and transducer array structure can be simplified to fewer, or even to one, transducer for applications where temperature measurement, but only a minimum or no identifying code capability, is required. Two such simplified structures are shown diagrammatically in FIG. 9 and FIG. 10. In the structure of FIG. 9, use is made of two surface acoustic wave reflectors 61 and 62 which return acoustic pulses to the single acoustic wave launching and receiving transducer 60. Measurement of the RF phase difference $\phi$ between reply pulses reflected from reflector 62 and reply pulses reflected from reflector 61, $\phi$ being equal to $4\pi(L_2-L_1)/\lambda$ rads, where $L_2$ and $L_1$ are the spacings from the centre-line of transducer 66 to reflectors 62 and 61 respectively and $\lambda$ is the surface acoustic wave wavelength, provide a measurement of the temperature of the label in the way previously described. In the structure of FIG. 10, The surface acoustic wave is constrained by suitable grooves 66, etched in the surface of substrate 63, to propagate around a circular, or "rat-race" propagation path so as to repetitively excite the single acoustic wave launching and receiving transducer 64. Measurement of the RF phase difference $\phi$ between successive reply pulses, $\phi$ being equal to $2\pi D/\lambda$ rads, where D is the diameter of the circular propagation path and $\lambda$ is the surface acoustic wave wavelength, again provides a measurement of the temperature of the label in the way previously described.

We claim:

1. Apparatus for remote temperature reading comprising transmitter means for transmitting electro-magnetic signals, label means adapted for attachment to or implantation in an article or animal for receiving a signal transmitted from said transmitter means and for retransmitting a reply, and receiver means for receiving and processing the reply; said label means including antenna means for receiving said transmitted signal, transducer means for converting said electromagnetic signal to a surface acoustic wave, a path on said label over which said surface acoustic wave travels, the time of travel of said surface acoustic wave over said path being a function of the temperature of the path, the same or further transducer means being arranged to convert said surface acoustic wave to a first electromagnetic signal after it has travelled over a first part of said path and to feed said signal to said antenna means for retransmission to said receiver means and thereafter to convert said surface acoustic wave to a second electromagnetic signal after it has travelled over a second part of said path and to feed said second electromagnetic signal to said antenna means for retransmission to said receiver means, said receiver means including circuitry for measuring the time interval between said first and second electromagnetic signals resulting from the passage of said surface acoustic wave over said path and for providing from said measured time interval an output indicative of the temperature of the environment of the label means.

2. Apparatus as claimed in claim 1 wherein said label means includes a plurality of transducer means at coded locations along said path arranged for retransmitting to said receiver means a coded sequence of electromagnetic signals indicative of an article or an animal to which said label is affixed or in which it is implanted.

3. Apparatus as claimed in claim 1 or 2 wherein the transmitter means is constructed and arranged to transmit electromagnetic signals in the form of pulses of radio frequency energy and the receiver is constructed and arranged to receive reply signals in this form and to measure the time interval between said first and second electromagnetic signals by measurement of the change in phase between said signals resulting from the passage of said surface acoustic wave over said path.

4. Apparatus as claimed in claim 1 wherein the said path is closed on itself and a single transducer means is included in said path.

5. Apparatus as claimed in claim 1 wherein a single transducer means is provided in said path having reflector means provided on each side of it, said reflector means being at different distances from the transducer means, said path extending between said reflector means.

* * * * *